United States Patent [19]
Castagner

[11] Patent Number: 5,591,902
[45] Date of Patent: Jan. 7, 1997

[54] DYNAMIC PYROTECHNICAL PENETROMETER

[76] Inventor: Bernard Castagner, 4, chemin de Bourgogne, F-77450 Coupvray, France

[21] Appl. No.: 411,096

[22] Filed: Mar. 27, 1995

Related U.S. Application Data

[63] Continuation-in-part of Ser. No. 75,546, filed as PCT/FR91/00997 Dec. 10, 1991, abandoned.

[30] Foreign Application Priority Data

Dec. 12, 1990 [FR] France .................................. 90 15512

[51] Int. Cl.⁶ ............................................. G01N 3/40
[52] U.S. Cl. ....................................... 73/84; 73/82
[58] Field of Search ............................ 73/79, 81, 84, 73/82, 78, 85, 12.08, 12.01, 12.09, 12.11

[56] References Cited

U.S. PATENT DOCUMENTS

| | | |
|---|---|---|
| 3,159,025 | 12/1964 | Pais . |
| 3,942,368 | 3/1976 | Hoyt . |
| 3,946,598 | 3/1976 | Towne et al. . |
| 4,034,603 | 7/1977 | Leeb et al. . |
| 4,390,307 | 6/1983 | Rice ........................................ 405/228 |
| 4,665,791 | 5/1987 | Bugiel ........................................ 89/1.1 |

FOREIGN PATENT DOCUMENTS

| | | |
|---|---|---|
| 0389375 | 9/1990 | European Pat. Off. . |
| 2290660 | 6/1976 | France . |
| 2584186 | 5/1989 | France . |
| 3834846 | 4/1990 | Germany . |
| 60-88349 | 5/1985 | Japan . |
| 62-245137 | 10/1987 | Japan . |
| 992656 | 1/1983 | U.S.S.R. . |
| 1079748 | 3/1984 | U.S.S.R. . |

*Primary Examiner*—Hezron E. Williams
*Assistant Examiner*—Nashmiya Ashraf
*Attorney, Agent, or Firm*—Young & Thompson

[57] ABSTRACT

The dynamic pyrotechnical penetrometer enables to determine the features of the soils by continuous detection and measurement of penetration of a probe rod (1) using the pressure created by a pyrotechnical gas generator (5). A standard probe rod (1) mounted on a piston (2) is placed in an amagnetic tube equipped with solenoids. This probe rod accommodates a magnet (3) on the one hand and a recoiling mass (4) on the other, which balances the amount of movement of the rod created by the gases of a pyrotechnical generator (5) contained in this recoiling mass. A unit for acquiring and processing the movement of the standard rod enables to calculate the resistance of the soil to the penetration of the rod.

13 Claims, 11 Drawing Sheets

DYNAMIC PYROTECHNICAL PENETROMETER

This application is a continuation-in-part of application Ser. No. 08/075,546 filed as PCT/FR91/00997 Dec. 10, 1991 now abandoned.

BACKGROUND OF THE INVENTION

The invention relates to a soil recognition and characteristic measurement device. The two main existing soil recognition systems are pressuremetry and penetrometry, especially dynamic penetrometry. The principle of dynamic penetrometry is to determine the kinetic energy necessary to insert a probe into the ground to a certain depth, whereas the kinetic energy is generally created by the standard drop of a given mass.

The drillings carded out with this system take up a long time and now that labor costs are high, the drillings are costly.

Moreover, most of these systems do not integrate automatic written report of the soils characteristics, which would confer increased credibility to the recognitions performed.

SUMMARY OF THE INVENTION

The dynamic pyrotechnical penetrometry device of the present invention enables to respond to these major requirements more specifically: execution speed, cost reduction and measurement credibility.

The device according to the present invention determines the soil characteristics by detection and continuous measurement of a standard probe rod inserted into the ground. This penetration is performed by using the pressure produced by a pyrotechnical gas generator.

The originality of the device of this invention will be demonstrated by its description, the justification of the techniques used and its operating diagram.

The most important features of the invention are as follows:

Use of the pressure created by a pyrotechnical gas generator in an ejection tube in order to drive a standard probe rod into the soil.

Continuous detection of the movement of the rod inside the ejection robe, especially by the passage of a magnet associated with the rod in solenoids located along the ejection tube.

Continuous calculation, using a pre-programmed electronic circuit, of the accelerometric resultant of this movement, which is the resultant of the acceleration created by the gas pressure on the rod and of the acceleration created by the resistance of the soil on said rod.

In the case of the light and portable system, use of the balance of the movement quantities by a vertical recoiling mass, a portion of which serves preferably as a gas expansion chamber and as a guide for the standard rod.

The invention further concerns an apparatus for soil recognition and characteristic measurement comprising a device of the invention. Advantageously, the apparatus is mobile, and more advantageously, it is fitted with caterpillar tracks.

BRIEF DESCRIPTION OF THE DRAWINGS

The following description is purely illustrative and non-limitative. It must be read in respect to the appended drawings of which.

DETAILED DESCRIPTION OF THE INVENTION

Figure 1:
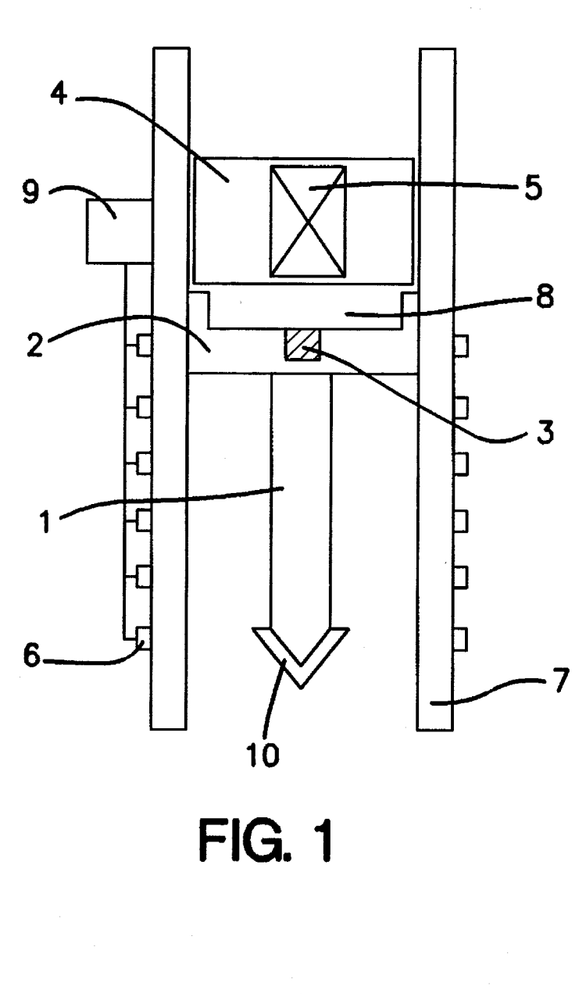
FIG. 1 represents the simplest expression of the device of the invention.

The standard probe 1 is mounted on a piston 2 on which a magnet 3 is placed.

The recoiling mass 4 balances the quantity of movement which will be transmitted to the standard rod 1 and to its piston 2.

A gas generator 5 is provided on this one. The energy absorption of the recoiling movement is ensured by gravity.

Within the scope of the invention, another means can be used to balance the stresses of the recoiling movement, such as energy dampers, the mass of the carrier or of the system.

The assembly comprised of the rod, the piston, the recoiling mass and the generator is located in a recoiling tube 7 made of amagnetic materials. The recoiling tube 7 is fitted with solenoids 6 preferably located at regular intervals and concentrically with respect to the launching tube.

These solenoids 6 are linked to the electronic and computerized data processing unit 9.

After start-up, the gas generator discharges into the expansion chamber 8 located between the piston 2 and its recoiling mass 4, whereas the pressure thus generated accelerates the standard rod 1. As the rod is ejected, the passing of the magnet 3 through the various solenoids 6 generates electric signals whose intervals of occurrence are calculated.

This enables to calculate the speed, then the acceleration of the standard rod.

The pressure P(t) discharged by a given gas generator in the expansion chamber is known either accurately by measurement, or with a good approximation (2 to 3%) because of the reproducibility of the performances of the gas generator used.

The deceleration force caused by the resistance of the soil to the penetration of the standard rod is thus known. It is equal to the difference between a first force $F_1(t)$ acting upon the standard rod 1 in order to push it into the soil, on the one hand, and a second force $F_2(t)$ opposed to the rod by the soil and slowing down the rod until its complete stopping.

$$R(t) = F_1(t) - F_2(t)$$

or, since $$F_1(t) = s \cdot P(t) \text{ and } F_2(t) = m \cdot G(t),$$

as $$R(t) = s \cdot P(t) - m \cdot G(t),$$

wherein

R(t) is the deceleration force, s is the cross-sectional area of the standard rod, P(t) is the pressure discharged by the gas generator, m is the mass of the standard rod, and G(t) is the acceleration of the standard rod.

The calculations are performed either with an appropriate logic circuit, or with an existing pre-programmed computer.

Figure 5:
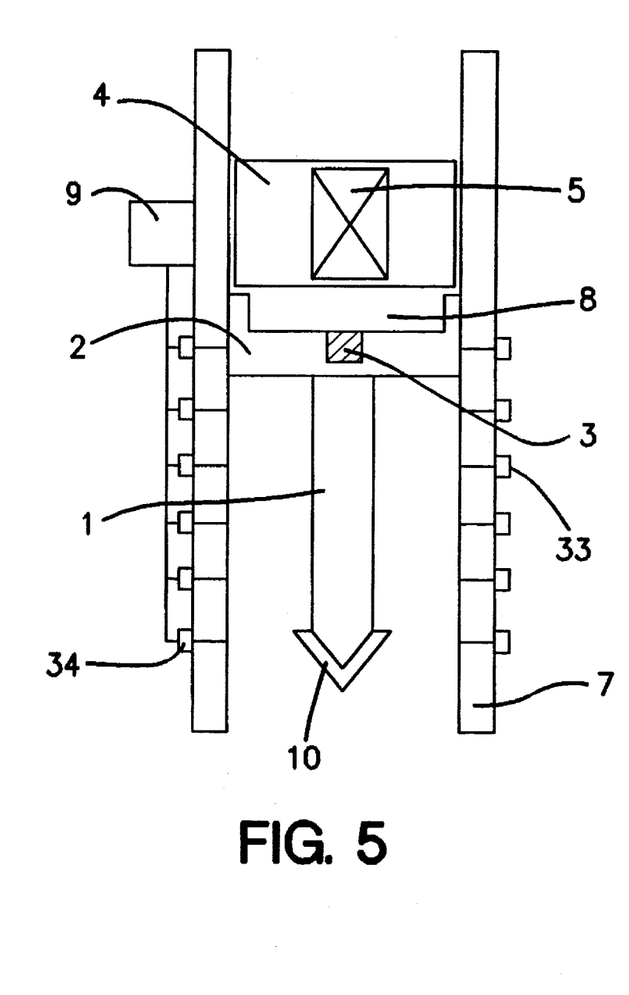
FIG. 5 represents a first embodiment of the device according to the invention.
Figure 6:
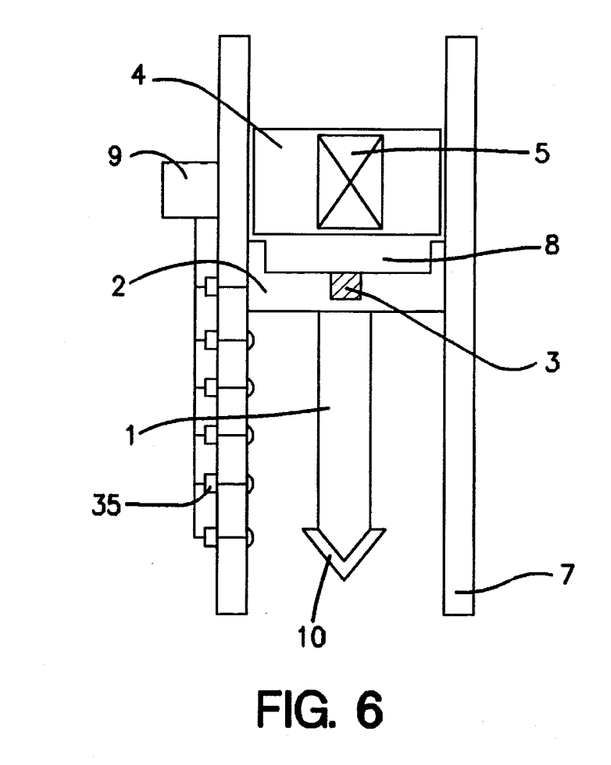
FIG. 6 represents a second embodiment of the device according to the invention.

Within the scope of the invention, other passage detection systems of this type can be used, such as electromechanical contactors 35 or photo-electric cells 34, as shown in FIGS. 5 and 6. Each photo-electric cell 34 cooperates with a light source 33. The light sources and the corresponding photo-electric cells are mounted in diametrically opposite positions and regularly spaced on the outer surface of recoiling tube 7. Appropriate holes are provided in the tube wall in order to allow for emission and, respectively, reception of light as the standard rod 1 passes in front of said holes.

Correspondingly, the electromechanical contactors 35 are mounted inside the recoiling tube 7 at regular intervals and operated by the rod 1 as it passes by.

Moreover, without departing from the scope of the invention, the passage detectors and a portion of the data processing circuit can be replaced with an accelerometer.

According to the type of measurement to be performed, the standard rod can be provided with a protruding tip (10).

Figure 2:
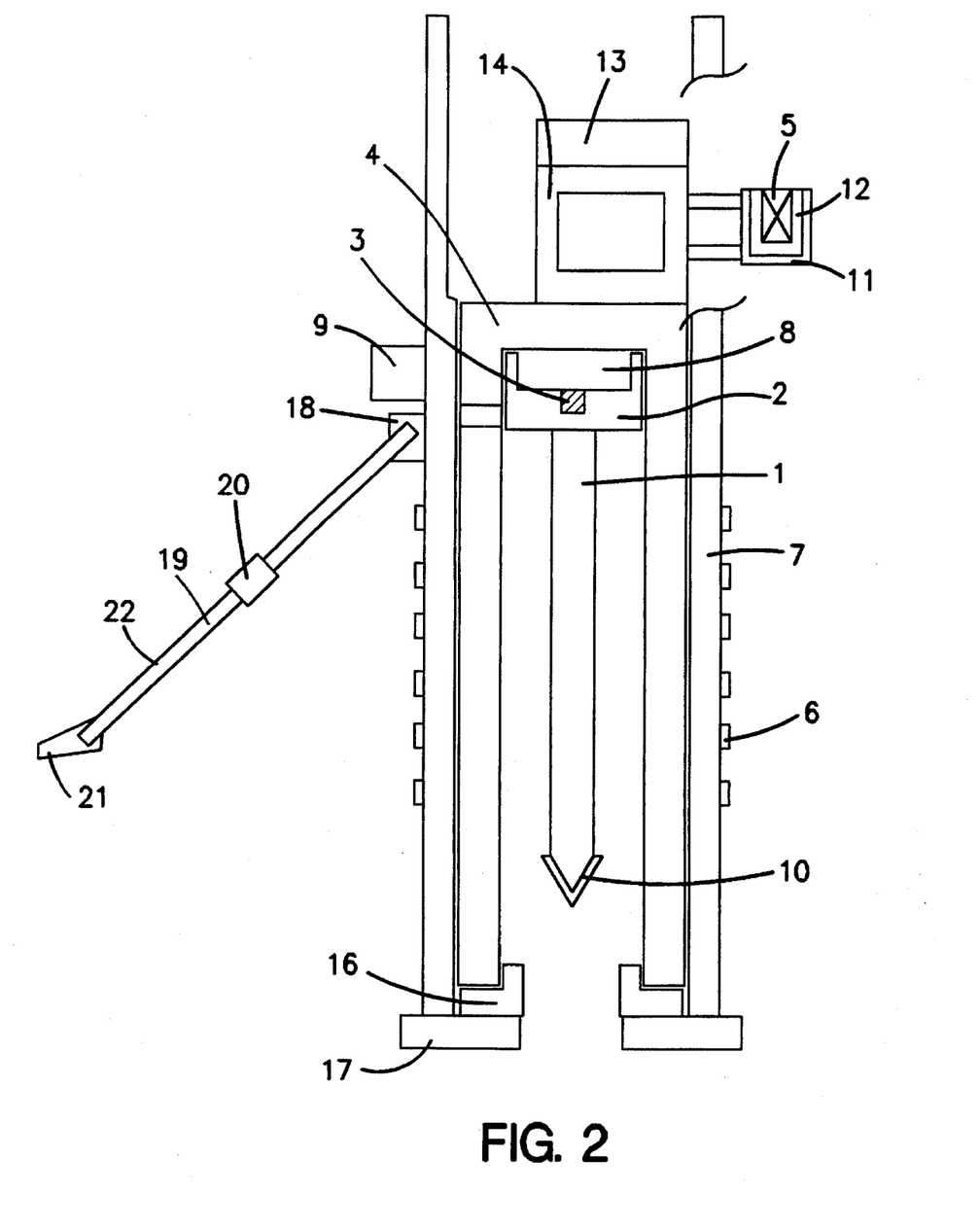
FIG. 2 represents an apparatus more especially suited to shallow drillings.

The device of this invention in its portable and operating version for shallow drillings is illustrated in FIG. 2.

The standard probe rod 1 is attached by a piston 2 inside which a magnet has been placed.

The recoiling mass 4 balances the amount of movement transmitted to the standard rod and to its piston. It is preferably made of a tube in amagnetic materials, for instance a cylindric tube closed at its upper end, whereas the recoiling mass serves as an ejection tube.

Before penetration, the standard rod fitted with the piston is retained in the recoiling mass, preferably using a deformable clip, but within the scope of the invention, another fastening system can be used, such as ball spring, leaf spring, or the like.

The recoiling mass 4 slides in a recoiling tube 7 made of amagnetic materials, preferably fiberglass composite with a duroplastic or thermoplastic matrix.

At its contact level with the soil, the guiding tube is preferably provided with a bearing heel 17 equipped with a recoiling mass fall damper 16.

The solenoids 6 used to detect the passage of the magnet are located preferably around the guiding tube and linked to the electronic processing unit 9.

The device can be autonomous and easily fitted with a collapsible and adjustable tripod 22.

This tripod can comprise an assembly ring 18 of three feet 19 (only one of which is shown) adjustable in length through, for instance, a lockable slide 20 and bearing on the ground using pads 21 that can be drilled for possible attachment of the system to the ground.

The recoiling mass is preferably located under the yoke support 14 of the gas generator and its triggering safety system 13.

The gas generator is preferably triggered mechanically using a hammer or the like but within the scope of the invention, electric or laser-beam triggering can be used.

The body of the gas generator is preferably made of thermoplastic, duroplastic, elastomer, cardboard or composite materials. For safety reasons, in case of accidental ignition outside its operating housing or in case of fire, the structure is preferably designed for opening up at low pressure.

In order to facilitate the loading sequence and to ensure safety, the gas generator 5 is preferably located inside a housing 12 situated in a mobile yoke 11.

The insertion of this mobile yoke 11 into its support 14 enables to place the gas generator in operating position, facing the intake channel of the expansion chamber 8 and to set the triggering safety system 13.

Without departing from the scope of the invention, other constructions for carrying out the "piston/ejection" function may be contemplated.

Figure 3:
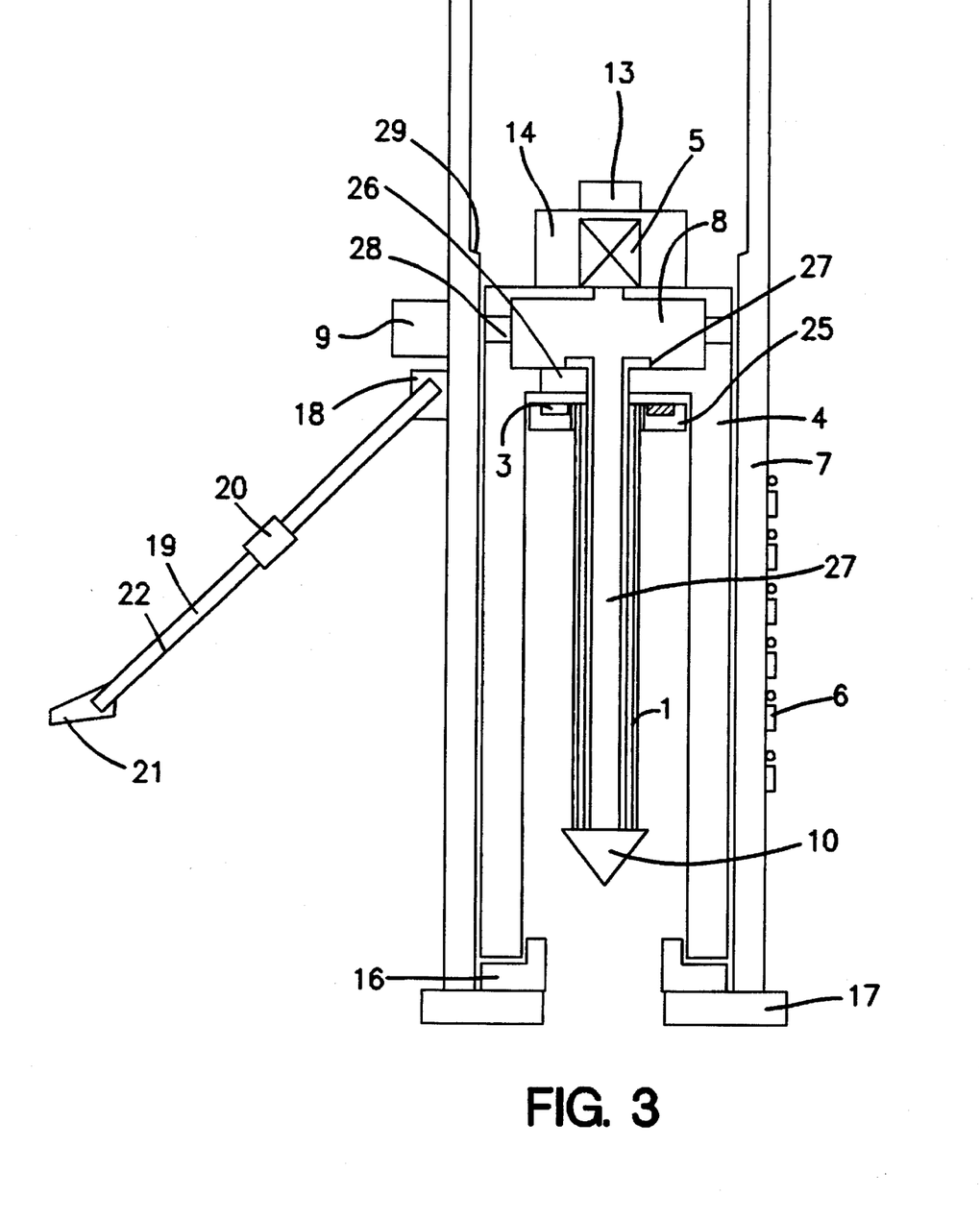
FIG. 3 represents an apparatus more especially suited to deeper drillings.

FIG. 3 provides an alternative embodiment especially suited to deep probing performed with only one standard rod or several rods which are assembled as the probing proceeds.

The push/ejection function and the guiding function of the standard rod are not ensured by a piston but on the one hand by the closed tip of the hollow standard rod 1 carrying the protruding or non-protruding tip 10, and on the other, by an axial tube along which the standard rod is sliding.

The standard probe rod 1 is fitted with a heel 25 which enables to limit its penetration into the soil, in case of excessive energy with respect to the energy absorbed by the penetration in the soil.

The magnets 3 are located in this heel 25. In this case, the solenoids are not concentric to the tube but located along the tube and the magnets placed on a plane perpendicular to the movement of the rod.

The standard probe rod slides around a guiding tube 27 which is linked, preferably using a chuck 26, to the recoiling mass 4, also serving as a recoiling guide and fitted with the expansion chamber 8 and the yoke of the gas generator 5. Within the scope of the invention, the probe rod 1 can be inside the guiding tube 27.

The recoiling tube 7 exhibits a bore 29 in its upper part.

The expansion chamber exhibits one or several holes 28 fitted or not with shearing membrane or flap.

Indeed, should the standard probe rod be blocked in the soil, the gases must be discharged from the expansion chamber in order to restrict the rise-up of the recoiling mass.

This discharge will be performed preferably using this bore 29 and its holes 28. They are situated so that they reduce the performances of the gas generator only marginally.

The recoiling tube 7 and the tubular portion of the recoiling mass exhibit an aperture 23 (FIG. 4) in order to enable loading the standard rod 1 equipped with its guiding tube 27. This aperture is closed during operation, either by a gate 30 or by rotation of the recoiling mass inside the guiding tube.

Figure 4:
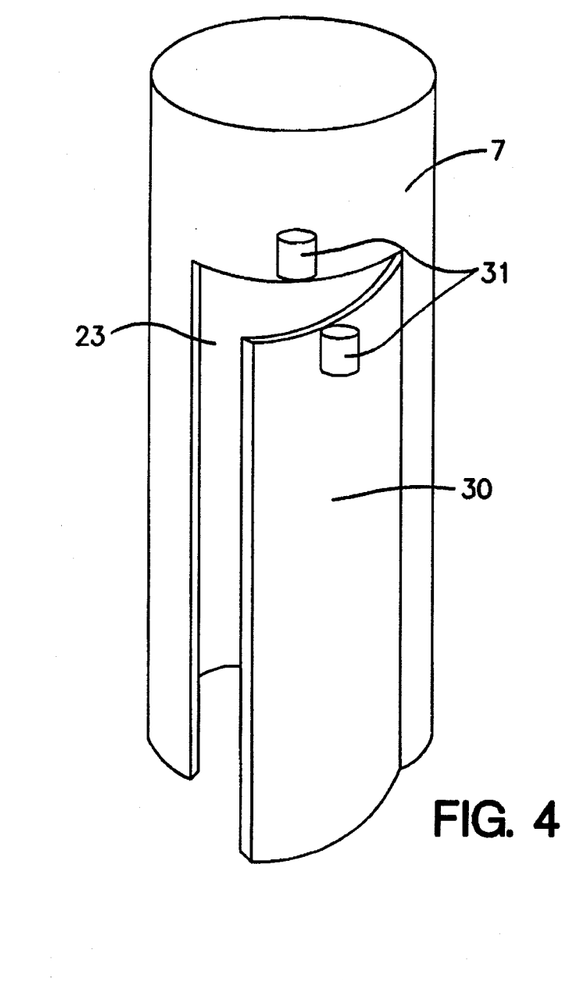
FIG. 4 represents the recoiling tube of the system according to FIGS. 1 to 3.

In case of a gate, loading the standard rod is done by opening gate 30 of the recoiling mass. Gate 30 is provided with a locking system 31 which is, for safety reasons, linked to the ignition safety device 13.

In case of partial or difficult penetration of the standard rod, it can be removed easily or plunged further by using a second gas generator.

In order to remove the standard probe rod 1, it suffices to open the chuck 26, the guiding tube 27 falls on the bottom of the standard rod, the system can then be released, the probe extracted, if needed, using an extractor bearing against the heel 25.

A second probe rod can be added to probe deeper, while attaching it in place of the heel after disassembly of the guiding tube.

The soil recognition and characteristic measurement system can be mounted on a vehicle and especially on an automotive vehicle. However, it is also conceivable to mount the device of the invention on a mobile carrier enabling to displace average size systems more easily according to the invention. The description below, by reference to FIGS. 7 to 23, relates to such a mobile device, designated hereafter as the vehicle according to the invention.

Figure 7:
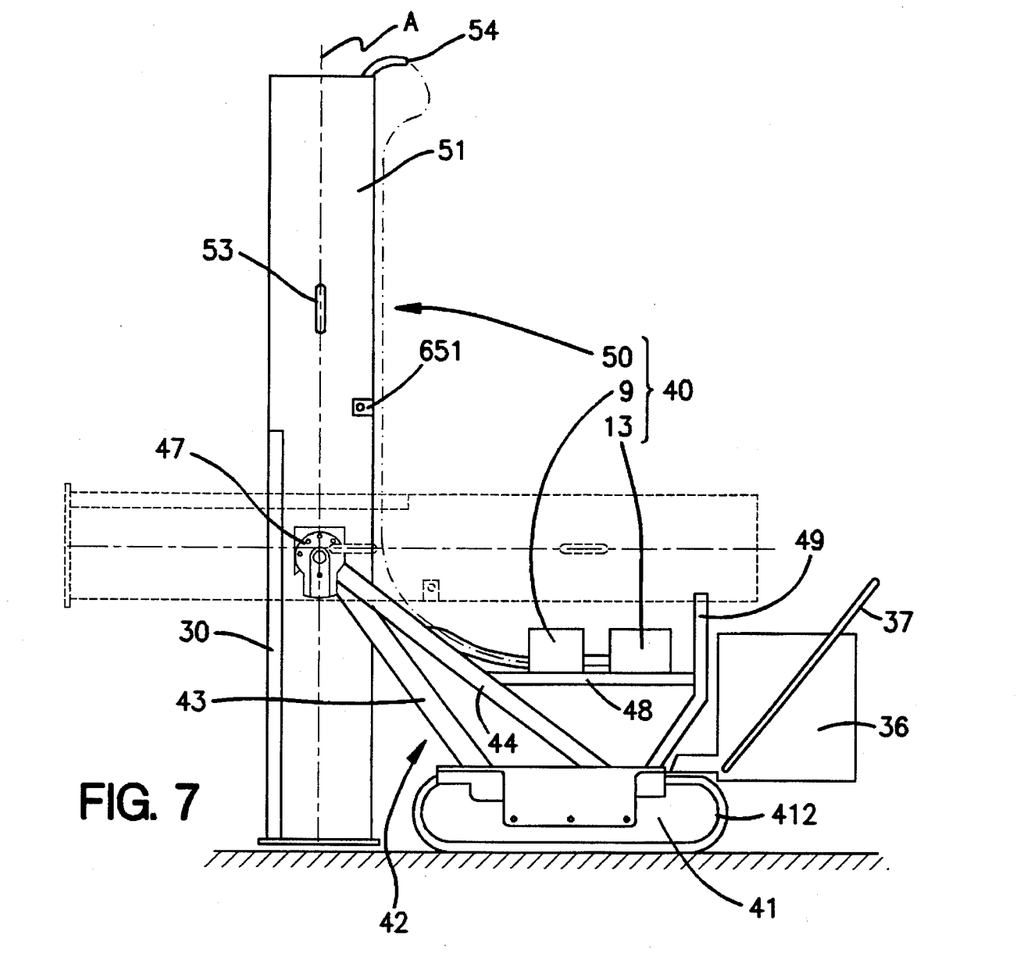
FIG. 7 represents a side view of a mobile apparatus containing the device according to the invention.
Figure 8:
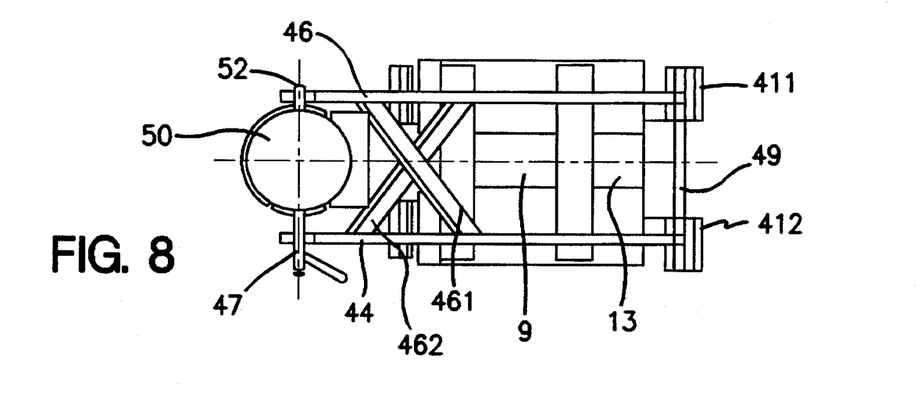
FIG. 8 represents a view from above of the apparatus of FIG. 7.

The soil recognition and characteristic measurement vehicle comprises a device 40 for soil recognition and measurement of their characteristics according to the invention, as well as a mobile carrier 41 fitted with caterpillar tracks 411, 412 and an interface frame 42 using which the device 40 is pivot-mounted on the carrier 41.

The device 40 may pivot between a horizontal transport position and vertical position and probing positions which are more or less vertical. Pivoting between horizontal transport position and a probing position which need not be perpendicular to the transport position enables to place the device 40 in an optimum probing position regardless of the position of the carrier 41, depending on the form of the soil around the probing area.

The interface frame 42 comprises two pairs of retaining arms 43, 44 and 45, 46 each pair of which describes a plane parallel to the other and which are mounted at a transversal distance on the carrier 41 so that the lower ends of the arms are mounted on the carrier 41 and that the upper ends meet in order to describe a junction bridge linked with the corresponding junction point of the other pair of arms by an axle 52. Both pairs of retaining arms are interlinked by two cross bracings 461, 462. The device 40 is mounted between both pairs of retaining arms in such a way that it may pivot around the axle 52. Blocking the device 40 in the horizontal transport position or in a probing position is performed using a blocking device 47 mounted on one of the pairs of retaining arms. In the embodiment represented, the blocking assembly 47 is mounted on the pair of arms 43, 44.

The recognition and measurement device 40 comprises a launching system 50 which contains all the elements forming the device 40, with the exception of the electronic and computer control box 9 and of the ignition casing 13, which are connected to the launching device 50 by an electric linkage 54 and which have been arranged on a plate 48 of the carrier 41. The electric linkage 54 comprises cables of two different electric circuits. One circuit includes all safety devices and the ignition casing 13. The other circuit includes the means for measuring movement of the standard rod during a probing shot.

The displacements of the recognition and measurement vehicle are performed by means of an engine 36 mounted on the carrier 41. Steering of carrier 41 is done by means of a handle 37. The carrier 41 has also been fitted with a support 49 for the launching system 50 when it is pivoted to the horizontal (or transport) position.

Figure 9:
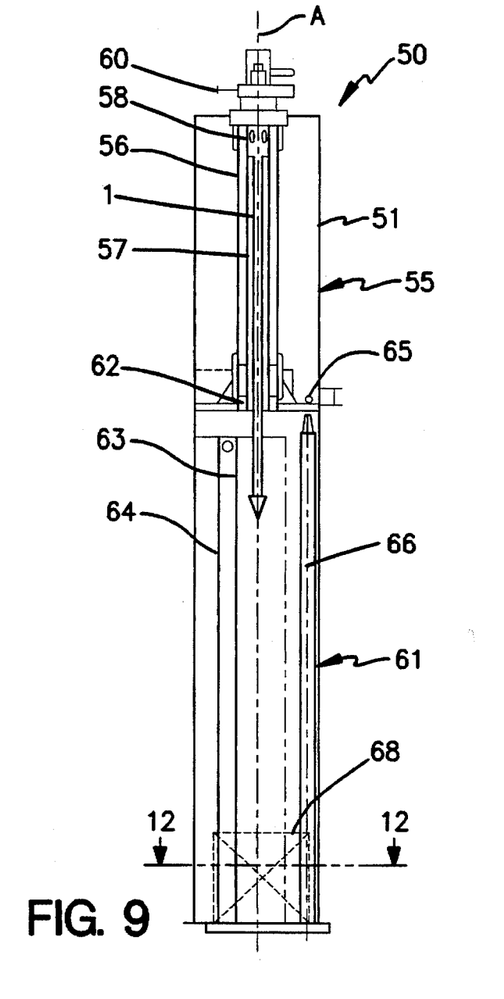
FIG. 9 represents a longitudinal section of the main elements of a launching device which is integral to the device according to the invention.
Figure 10:
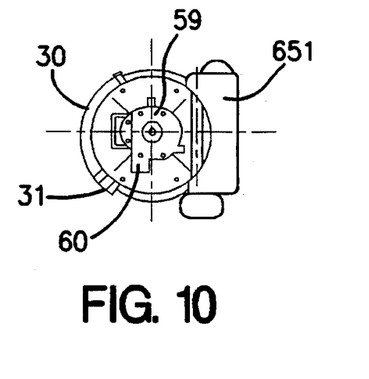
FIG. 10 represents a view from above of the device of FIG. 9.
Figure 11:
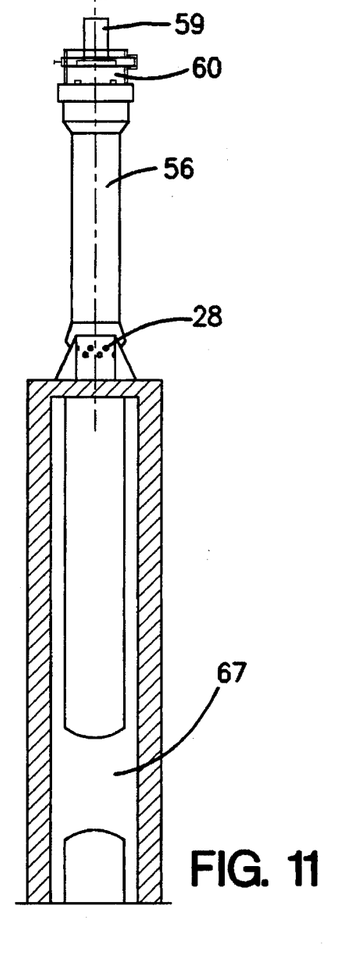
FIG. 11 represents a side view of a ballast weight and of a launching tube fitted with the device of the invention.

The launching device 50 comprises a shaft 51 forming the envelope of the launching device 50. The shaft 51 has more or less the shape of a revolution cylinder developing around a longitudinal axis A. The shaft 51 is fitted with a toggling handle 53 designed to facilitate changing the position of the launching device 50 and a gate 30 arranged in the lower part of the shaft 51, considered in the probing position of the said shaft. The gate 30 is pivot-mounted around an axis parallel to the longitudinal axis A of the shaft 51 and is intended to facilitate the loading of the launching device 50 with the reference probing rod 1. The gate 30 is kept closed by a latch 31 fitted with a safety sensor 32 intended for guaranteeing that the latch 31 has been closed. The safety sensor 32 is connected electrically to the ignition casing 13.

The launching device 50 comprises, inside the shaft 51, in an upper part 55, considered in a probing position of the device 50, a first launching tube 57 arranged coaxially with respect to axis A and exhibiting a minimum diameter suited to the calibre of the reference probing rod 3. The launching tube 57 has been arranged inside a second launching tube 56 with maximum diameter and maintained by a locking ring 571. The shaft 51 comprises, moreover, close to its upper end, retaining clips 58 of the piston 2 of the reference probing rod 1.

An actuation or ignition device 59 and a yoke 60 have been arranged coaxially on the upper end of the shaft 51. The ignition device 59 is intended for triggering the pyrotechnic gas generator 5 as well as a probing shot of the reference probing rod 1.

In a lower part 61 separated from the upper part 55 by a bottom plate 62, the launching device 50 comprises a measurement tube 63 fitted with solenoids 6 and retained inside the shaft 51 by a support 64. The bottom plate 62 is maintained in raised position in relation to the lower end, viewed in the probing position of the launching device 50, by at least one shock-absorbing jack 66 attached to the lower end by a fastening stub 69.

Figure 12:
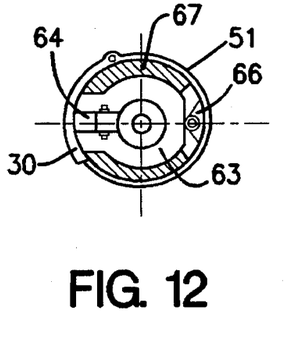
FIG. 12 shows a cross section F of the inner side of the device of FIG. 11.

As shown in FIG. 12, the gate 30 gives access to the inside of the shaft 51 and a ballast weight 67 which is oriented in such a way that it contributes to this access. The measurement tube 63, conversely, is oriented so that the full carrying part of the solenoids 6 is directed towards the gate 30 in order to give access to the solenoids 6, as well as to a signal acquisition box 70, linked electrically to the solenoids 6, and to cables 71 connected to the electronic and computer control box 9.

The shaft 51 is fitted, finally, with a locking rod 65 arranged in an insert 651 rigidly connected to the shaft 51.

Figure 13:
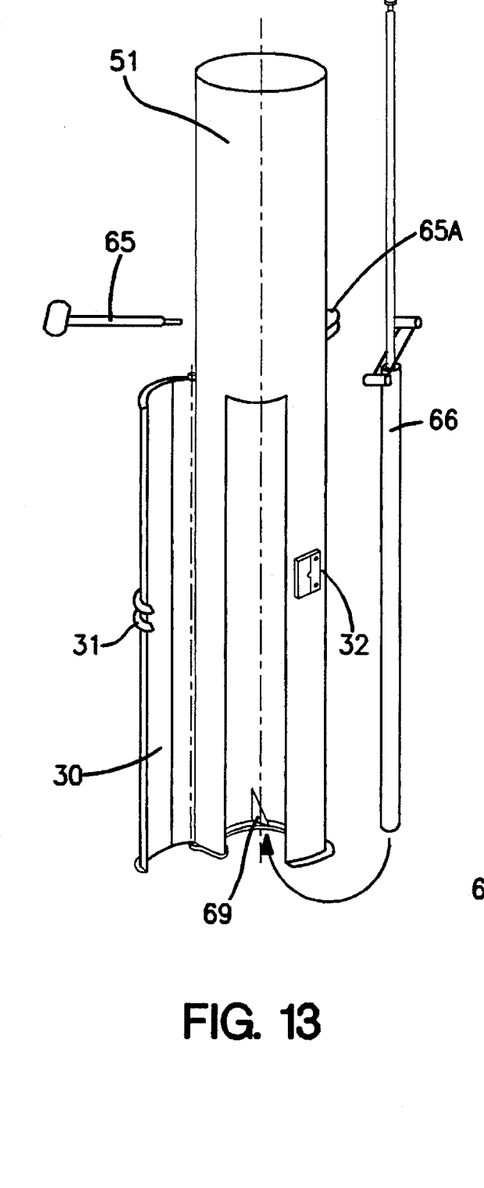
FIG. 13 represents an embodiment of the recoiling tube of FIG. 4.

FIG. 13 is an exploded view of the assembly of the shock-absorbing jack 66 inside the shaft 51 as well as of the positioning of the recoiling locking rod 65 and the gate 30 in open position.

Figure 14:
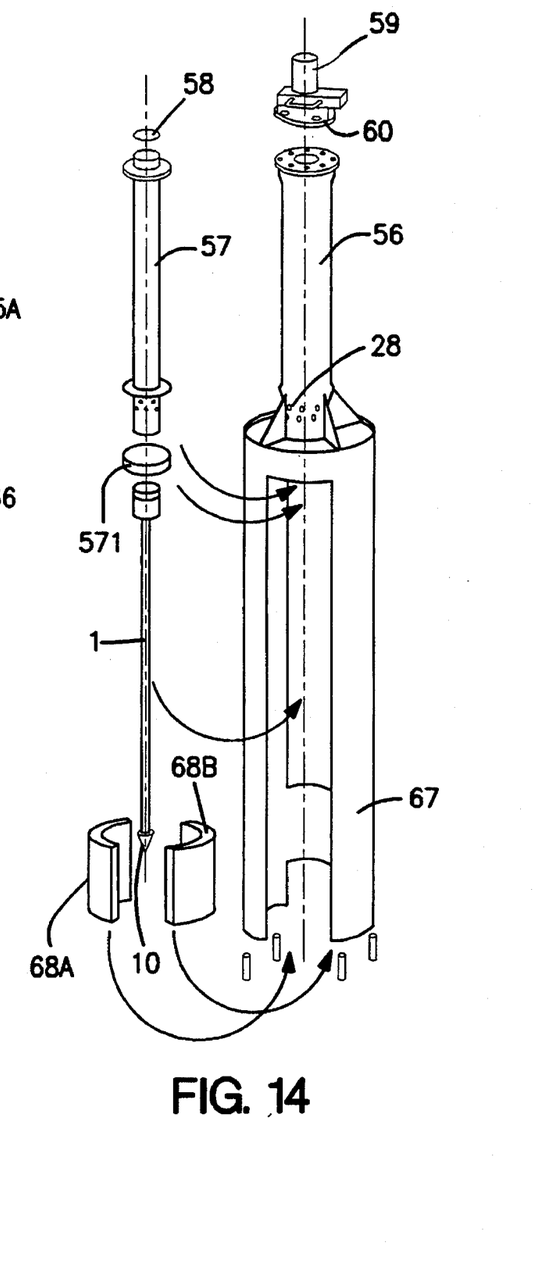
FIG. 14 is an exploded view of the ballast weight and of the launching tube of FIG. 11 together with a second launching tube and the probing rod according to the invention.
Figure 15:
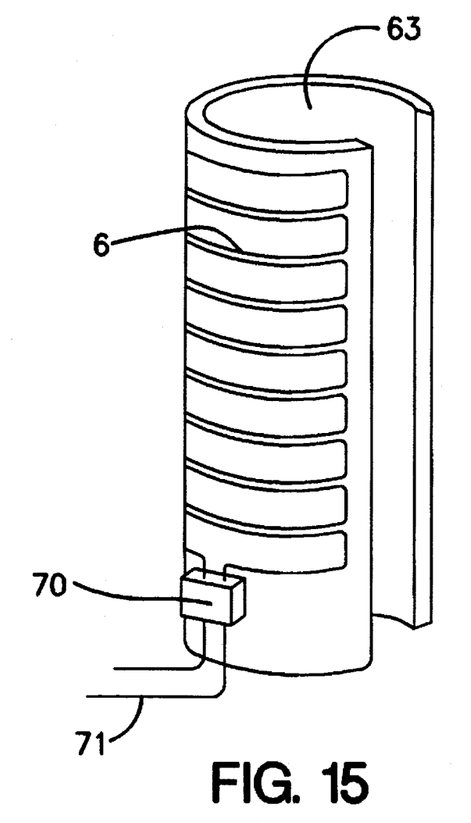
FIG. 15 represents a measuring tube fitted with solenoids.

FIG. 14 is an exploded view of the arrangement of the launching tube 56 with maximum diameter which is connected rigidly to the ballast weight 67, and of the arrangement of the actuation device 59 and the yoke 60 arranged axially above the launching tube 56, on the one hand, and of the arrangement of the launching tube 57 with minimum diameter and of the reference probing rod 1, as well as of the arrangement of additional ballast weights 68A, 68B of the retaining clip of the piston 58 located in a groove cut in the upper part of the launching tube 56 and 57 and a locking ring 72 of the launching tube 57 with minimum diameter, on the other hand.

The launching tube 56 is rigidly mounted to the ballast weight 67 and, thereby, permanently forms the recoiling mass 4. Contrarily to this, the additional ballast weights 68A and 68B are foreseen to be mounted only if a more powerful gas generator has to be used. The additional ballast weights then avoid any excess movement of the recoiling mass.

Figure 18:
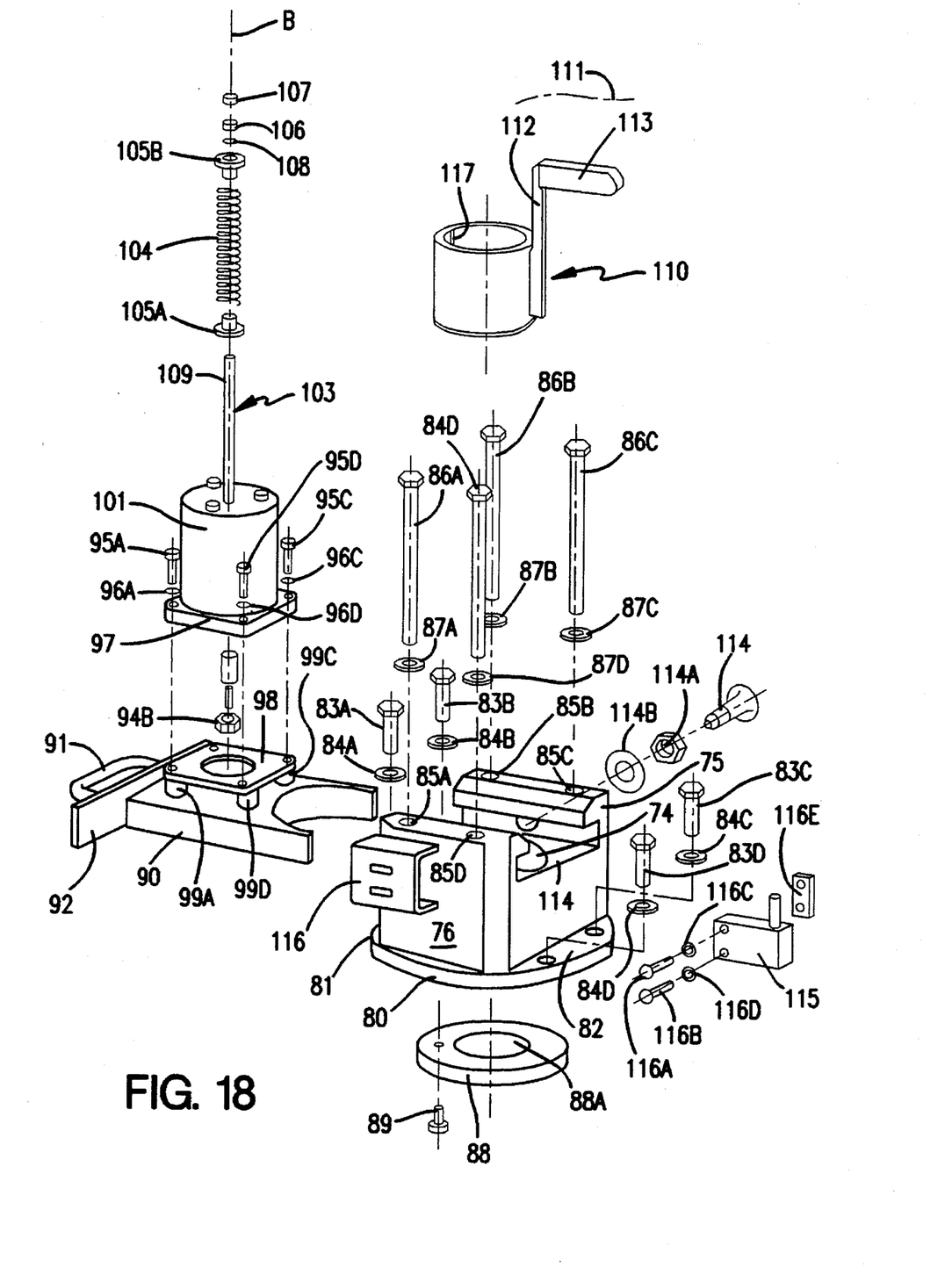
FIG. 18 is an exploded view of the actuation device and of the yoke of FIGS. 16 and 17.

The yoke 60 comprises a body 72 formed in a single piece by a block 73 which is more or less parallelipipedic in shape and empty in its center in order to exhibit a housing 74 designed for accommodating at least one gas generator 5. The parallelipipedic block 73 is raised on two of its parallel sides by two parallel panels 75, 76 formed in order to exhibit on their opposite surfaces, i.e. directed towards the axis D, grooves 77, 78 which are horizontal and designed for accommodating a locking slide valve of the yoke 60 carrying the actuation or ignition device 59. The yoke body 72 finally comprises, in one single piece, with the other parts of the yoke body, a base 80 with a circular periphery and exhibiting on both sides of the block 73 which are not topped by the panels 75, 76, shoulders 81, 82 wide enough so that two bores 81A, 81B and respectively 82A, 82B can be arranged on each of those shoulders. The bores 81A, 81B, 82A, 82B are intended for being traversed by the screws 83A, 83B, 83C, 83D, each fitted with a corresponding washer 84A, 84B, 84C, 84D when the yoke is mounted at the end of the launching tube 56.

The thickness of the panels 75, 76 is sufficient so that the bores 85A, 85B, 85C, 85D can be drilled, intended for accommodating the screws 86A, 86B, 86C, 86D fitted with washers 87A, 87B, 87C, 87D using which the yoke 60 has been fastened to the upper end of the launching tube 56.

The base 80 of the yoke body 72 is also formed in order to accommodate a diffuser 88 in the shape of a disk liable to be attached to the yoke body 72 using a screw 89. The diffuser 88 is fitted, in its center, with a series of openings 88A forming channels through which the gases produced by the gas generator 5 may exhaust to the expansion chamber 8.

The diffuser 88 is fastened to the yoke body 72 in such a way that the openings 88A of the diffuser 88 are located in pre-set positions in order to obtain optimum clearance of the gases towards the expansion chamber 8, as it will be explained below in more detail.

The closing slide valve 79 and the yoke 60 are formed by a plate 90 fitted with a handle 91 and a stopping plate 92 limiting the penetration of the slide valve 79 into the yoke body 72. The plate 90 carries the actuation or ignition device 59 mounted using four screws 95A, 95B, 95C, 95D, each fitted with a corresponding washer 96A, 96B, 96C, 96D, with a first flange 97 connected rigidly to the ignition device 59 and with a second flange 98 maintained on a parallel plane to that described by the plate 90 and at a distance from the former by the feet 99A, 99B, 99C, 99D. Besides, the plate 90 of the closing slide valve 79 exhibits a bore 100 whose axis corresponds to the axis D of the ignition device 59 and which is intended for the passage of a striking pin 94 actuated by the ignition device 59. The travel of the striking pin 94 can be adjusted by a setting screw 94A or a setting nut 94B.

Figures 16, 17:
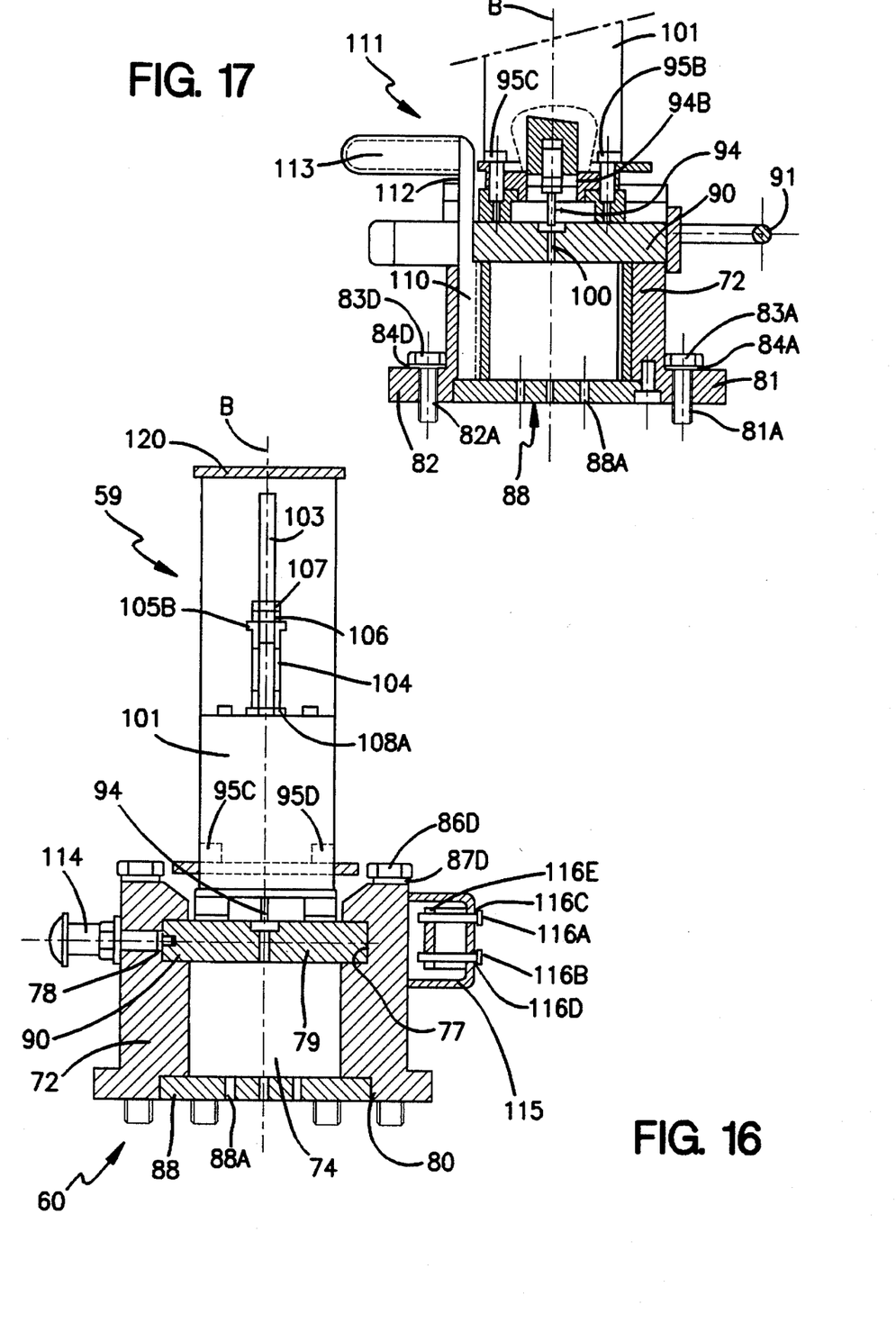
FIG. 16 represents, in a first longitudinal section, an actuation device for the apparatus of FIG. 7 and a yoke carrying this device.
FIG. 17 represents, in a second longitudinal section, an actuation device for the apparatus of FIG. 7 and a yoke carrying the device.

The actuation or ignition device 59 comprises an electromagnet 101 mounted inside a cylindrical revolution casing 101, developing around the axis D, connected rigidly in its lower base to the first flange 97 and carrying on its upper base 102 a rod 103 whose axis corresponds to the axis D of the ignition device 59 and which is fitted with a return spring 104 mounted coaxially on the rod 103 between two disks 105A, 105B whereby the disk 105A bears upon the upper base 102 of the electromagnet 101 and whereby the disk 105B bears upon the upper end of the return spring 104, using a nut 106 and a counternut 107, with the addition of a washer 108 and screwed onto a threaded part 109 of the rod 103.

The use of the nut 106 and of the counternut 107 on the rod 103 enables to adjust the return force of the rod 103.

Advantageously, the striking pin 94 is attached directly to the lower end of the rod 103, for instance by an outer thread on the rod 103 and a corresponding inner thread on the striking pin 94.

The gas generator 5 is implemented and removed after usage, using a modular extraction casing 110 of the gas generator. The modular casing 110 is fitted with a pick-up arm 111 fixed rigidly to the side wall of the casing 110 by one or two orthogonal branches 112, 113 forming the pick-up arm 111. The branch 112 is fixed to the protruding wall of the casing 110 and is inserted, when placing the casing 110 in the empty space 74 of the yoke body 72, into a slot 114 drilled into the yoke body 72 dedicated to this end. This arrangement precludes any rotation by the modular casing 110 which might take place when in the empty space 74.

The second branch 113 of the pick-up arm 111 is of sufficient length for easy handling of the modular casing 110 during positioning.

The inner wall of the modular casing 110 is fitted, besides, with a rib 117 parallel to the longitudinal axis of the casing 110. This rib 117, preferably located diametrically opposite the pick-up arm 111, is intended for ensuring good positioning of the gas generator 5 in the modular casing 110.

In order to monitor correct positioning of the locking slide valve 79, of the yoke 60, carrying the actuation device 59, the yoke 60 is fitted with a snap-on button 104 mounted on the panel 75 of the yoke body 72 where it is fastened using a nut 114A and a washer 114B with adequate shape and size.

The snap-on button 114 is designed for engaging into a blind hole 201 drilled into the side surface of the plate 90 engaged into the groove 78.

Moreover, the yoke 60 is fitted with a closing safety sensor 115 screwed on a support 116, fixed rigidly to the panel 76 of the yoke body 72, using two screws 116A and 116B and a flange 116E. The sensor 115 is linked electrically to the ignition safety device 13.

The actuation or ignition device 59 is protected when it is inserted into the yoke 60, by a protective guard 120 with a more or less cylindrical revolution shape, closed on one side and place on the device 59 by sliding it onto the box of the electromagnet 101 as with a sleeve or a cap.

Figure 19:
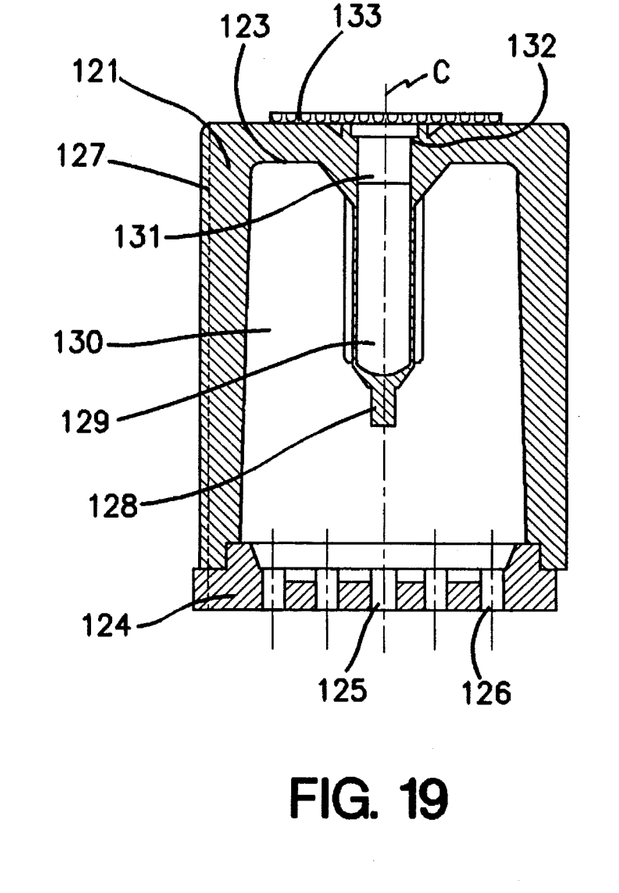
FIG. 19 represents the gas generator of the device according to the invention.

The gas generator 5 comprises a generator body 121 with the overall shape of a revolution cylinder with a side wall 122 and a first base 123 fixed rigidly to the side wall 122. The body 121 also comprises a second base 124 formed by a sealing cover fitted with a series of gas exhaust openings 125 as well as a series of sealing listels 126 whose number equals that of the openings 125. The gas generator 5 is designed for placement in the yoke 60 so that the sealing cover 124 is directed downwards and thus bearing onto the diffuser 88. In order to obtain maximum gas exhaust from the gas generator 5 to the expansion chamber 8, the arrangement of the openings 125 of the sealing cover 124 must correspond to the arrangement of the openings.

In order to benefit fully from this arrangement, the generator body 121 exhibits on its outer surface a groove 127 oriented parallel to the axis C of the gas generator 5. When placing the gas generator into the modular casing 110, the groove 127 works together with the rib 117 of the modular box 110. Thus, superimposition of the openings 125 of the sealing cover 124 and the openings 88A of the diffuser 88 is ensured.

The base 123 of the generator body 121 is pushed-in in its center and prolonged toward the inside of the generator body by a pipework 127 whose free end 128 is closed.

Thus, there is defined inside the generator body 121 a first volume 129 inside the pipework 127 and a second volume 130 between the walls of the generator body 121 and the pipework 127. Whereas the first volume is designed for accommodating the ignition powder, the second volume is designed for accommodating a fuel, such as for instance propergol.

In order to trigger the ignition of the gas generator 5, a primer 13 1 is located at the center of the base 123 and in contact with the ignition powder. The primer 131 is fitted with a sealing joint 132 for tightness between the penetration rims of the base 123 and of the primer 131. The primer 131 is crimped inside the base 123. Before usage, the primer is protected by a covering gum 133 laid and attached flat onto the base 123 of the generator body 121.

Figure 20:
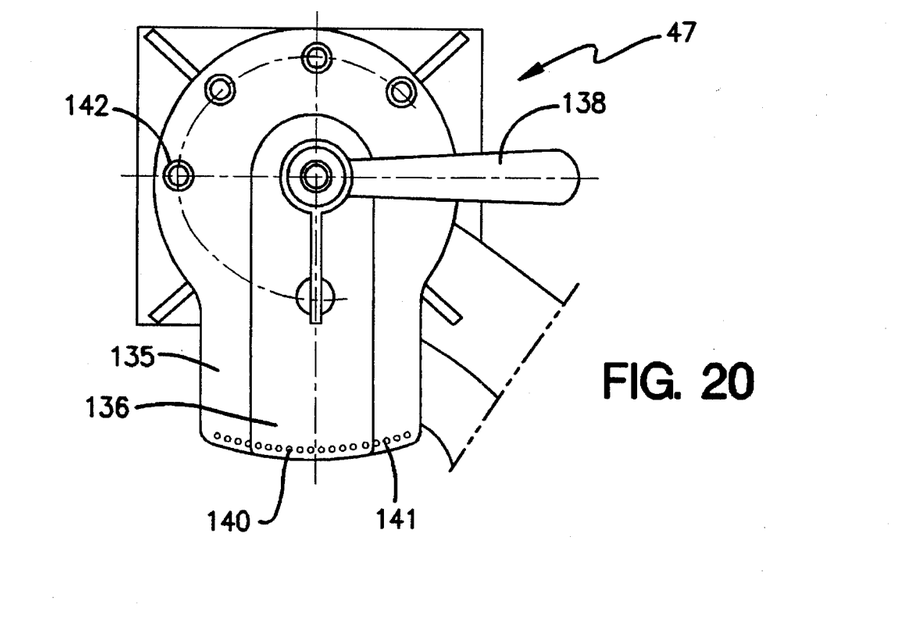
FIG. 20 represents the blocking device in position for the device represented in FIG. 7.
Figure 21:
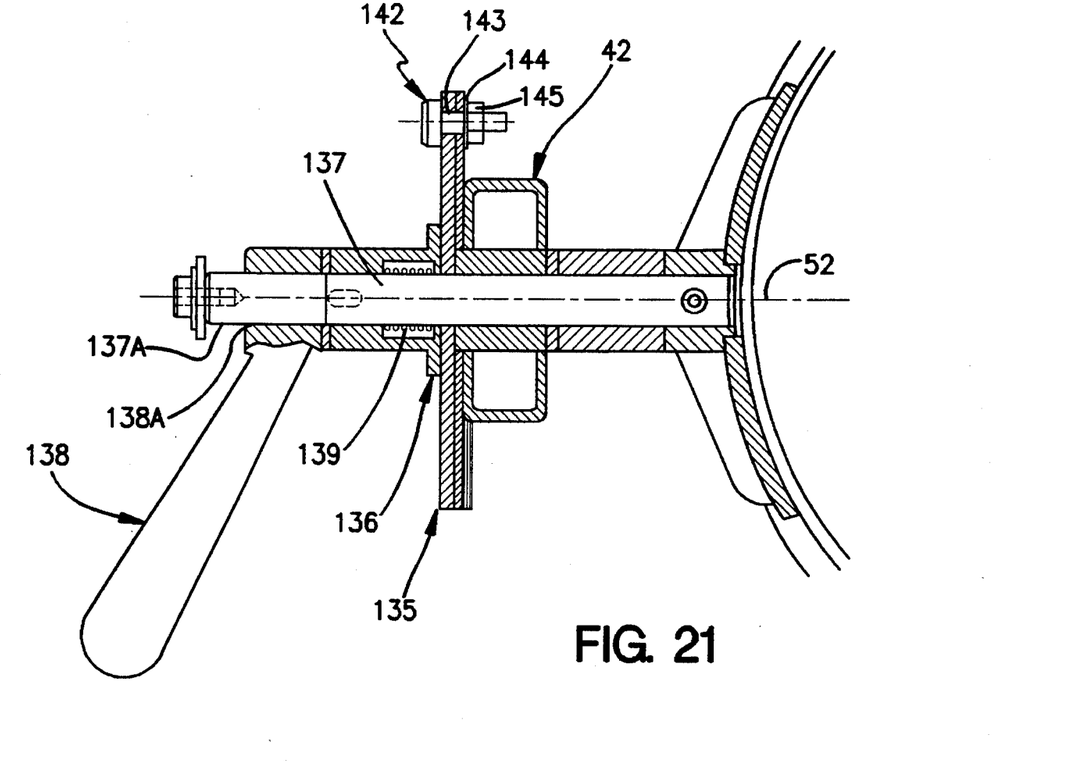
FIG. 21 represents a longitudinal section of the blocking device of FIG. 20.

The blocking device 47 which enables to stop the launching device 50 in a horizontal position, so-called transport position, or in more or less vertical probing position, comprises a fixed locking end plate 135 connected rigidly to the interface frame 42, a mobile end plate 136 mounted so that it can rotate around an axis 137 fixed rigidly to the interface frame 42 and a tightening handle 138 designed for pressing the mobile end plate 136 onto the fixed end plate 135 using the strength of a return spring 139 arranged coaxially on the axle 137 and between the fixed end plate 135 and the mobile end plate 136.

To this end, the fastening handle at the free end of the axle 137 is fitted with a thread 137A and the tightening handle 138 is fitted with a corresponding threaded bore 138B. Loosening and respectively tightening the mobile end plate 136 onto the fixed end plate 135 is obtained by rotating the tightening handle 138 as if it were a screw.

Positioning the mobile end plate 136 with respect to the fixed end plate 135 is made easier by the presence of centering studs 140 arranged on the mobile end plate 136 and oriented towards the fixed end plate 135, on the one hand, and the centering opening 141 arranged on the fixed end plate 135.

For increased safety during displacements of the recognition vehicle, the launching device 50 is fixed in its transport position not only by tightening the handle 138, but also by placing a centering pin 142 into the openings 143 and 144 drilled respectively into the mobile end plate 136 and in the fixed end plate 135 as well as by blocking the pin using a nut 145.

I claim:

1. Soil recognition and characterization device comprising:

a recoiling tube;

a probe rod constructed and arranged for movement with respect to the recoiling tube;

a pyrotechnical gas generator, detection means mounted on said recoiling tube and including several elements, said probe rod including means for penetrating soil by pressure produced by the pyrotechnical gas generator, and said elements including means for detecting the movement of the probe rod as said rod passes levels of the detection means, so as to provide a measurement of the probe rod movement during penetration of soil; and a recoiling mass located in the recoiling tube for balancing the amount of movements transmitted to the probe rod, the recoiling mass rising in and relative to the recoiling tube to absorb the reaction to the force applied by the generator to the probe rod.

2. Device according to claim 1, wherein the elements comprise solenoids located along the recoiling tube, and the movement of the probe rod is detected by the passing of a magnet associated with said rod, through the solenoids.

3. Device according to claim 1, wherein said means for detecting the movement of the probe rod comprise photoelectric cells or electromechanical contacts.

4. Device according to claim 1, wherein coordinates of the rod movement are introduced into a computer preprogrammed and initialized with parameters of the soil recognition and characterization device, in order to acquire soil characteristics directly and to make said characteristics available for display or printing.

5. Device according to claim 1, wherein the gas generator is implemented, and removed after use, in a modular extraction casing provided with positioning means.

6. Device according to claim 1, wherein the recoiling mass includes a portion which serves as a guiding tube for the probe rod and as an expansion chamber for gases generated by the pyrotechnical gas generator.

7. Device according to claim 1, wherein the recoiling mass comprises the housing of the pyrotechnical gas generator.

8. Device according to claim 6, wherein the expansion chamber includes at least one safety vent, and the recoiling tube includes a bore to facilitate exhaust of generated gases.

9. Device according to claim 1, wherein the probe rod is hollow and slides along a removable guiding tube.

10. Device according to claim 1, wherein the probe rod is comprised of several sections assembled by a locking-fitting.

11. Device according to claim 1, wherein the gas generator comprises a body made of thermoplastic or composite materials.

12. Soil recognition and characteristic measurement vehicle comprising a mobile carrier onto which a device according to claim 1 is mounted.

13. Vehicle according to claim 12, wherein the carrier is provided with caterpillar tracks.

* * * * *